United States Patent [19]

Brossmann et al.

[11] 4,381,222

[45] Apr. 26, 1983

[54] PROCESS FOR THE DISTILLATIVE SEPARATION OF TERTIARY ALKYL HYDROPEROXIDES AND DITERTIARY ALKYL PEROXIDES

[75] Inventors: Gottfried Brossmann, Höllriegelskreuth; Fritz Diem, Munich, both of Fed. Rep. of Germany

[73] Assignee: Peroxide-Chemie GmbH, Höllriegelskreuth, Fed. Rep. of Germany

[21] Appl. No.: 315,389

[22] Filed: Oct. 27, 1981

Related U.S. Application Data

[63] Continuation of Ser. No. 138,782, Apr. 10, 1980, abandoned.

[30] Foreign Application Priority Data

Apr. 24, 1979 [DE] Fed. Rep. of Germany ....... 2916572

[51] Int. Cl.$^3$ ............................................... B01D 3/34
[52] U.S. Cl. ........................................ 203/33; 203/36; 203/92; 203/95; 568/576
[58] Field of Search ................... 568/576; 203/34–37, 203/91, 92, 95, 33

[56] References Cited

U.S. PATENT DOCUMENTS 3,449,217 6/1969 Harvey ................................ 568/576

FOREIGN PATENT DOCUMENTS 1137717 3/1973 United Kingdom .

Primary Examiner—Frank Sever
Attorney, Agent, or Firm—Felfe & Lynch

[57] ABSTRACT

A process for the distillative separation of tertiary alkyl hydroperoxides of the formula

R—OOH wherein
R is a tertiary alkyl group with 4 to 6 carbon atoms from the corresponding di-tertiary alkyl peroxides resulting during their preparation, which process comprises neutralizing the reaction mixture resulting during the preparation of the tertiary alkyl hydroperoxide, subjecting same to vacuum distillation in the presence of water at a temperature of less than about 45° C. and recovering the purified tertiary alkyl hydroperoxide as a bottoms product.

10 Claims, No Drawings

PROCESS FOR THE DISTILLATIVE SEPARATION OF TERTIARY ALKYL HYDROPEROXIDES AND DITERTIARY ALKYL PEROXIDES

This is a continuation of application Ser. No. 138,782, filed Apr. 10, 1980, now ABN.

DESCRIPTION

The present invention relates to a process for the distillative separation of tertiary alkyl hydroperoxides of the general formula

R—OOH in which R represents a tertiary alkyl group, with 4 to 6 carbon atoms, from the corresponding di-tertiary alkyl peroxides resulting during their preparation, and especially, a process for the separation of tertiary butyl hydroperoxide from di-tertiary butyl peroxide.

The preparation of tertiary alkyl hydroperoxides takes place, in general, by means of the conversion of the corresponding alcohols with hydrogen peroxide and the use of acid catalysts, such as sulfuric acid, or by means of oxidation of the corresponding alkanes or alkenes. In all processes, undesirable byproducts are formed, which must be separated from the desired tertiary alkyl hydroperoxides.

Thus, in the preparation of tertiary butyl hydroperoxide by means of the conversion of tertiary butanol with hydrogen peroxide in the presence of sulfuric acid, the formation of undesired di-tertiary butyl peroxide is also catalyzed by the presence of the sulfuric acid. With these processes, purification took place, thus far, by means of the addition of potassium hydroxide, since it is possible to achieve a separation via salt formation. The disadvantage of this method, however, can be seen in the fact that, with this treatment, a considerable dilution of the desired tertiary butyl hydroperoxide takes place by means of potassium hydroxide, which creates transport problems, and secondly, forces the users of the hydroperoxide to start the preparation of perester with all neccessary alkali and tertiary butyl hydroperoxide already in the reactor. This is highly disadvantageous, since the various peresters are very easily saponifiable. If the tertiary butyl hydroperoxide, on the other hand, is to be used for the preparation of perketal, which takes place under acid catalysis, then neutralization of the potassium hydroxide is required first, which is also disadvantageous.

From German Pat. Spec. No. 23 49 737 a process for the preparation of alkyl hydroperoxides is known, according to which branched alkanes in a liquid state are oxidized with oxygen, whereupon the oxidation products are extracted with a polar extraction solvent, such as water. The present state of the art indicates that the hydroperoxides, which are extracted along with the carboxylic acids, can be recovered by carrying out an azeotropic distillation of the wash water. The present state of the art, however, does not indicate how the desired tertiary alkyl hydroperoxides can be separated from the undesired di-tertiary alkyl peroxides that are always formed as byproducts.

German Pat. Spec. No. 21 59 764 discloses a process for the continuous production and concentration of hydrocarbon hydroperoxides, according to which the oxidation of the corresponding hydrocarbons takes place simultaneously in the course of a rectifying distillation with a carrier gas. In this process, nitrogen, steam, nitrogen-steam mixtures, oxygen, or air can be used as the carrier gas. With this process, which is preferably carried out at normal pressure, the reactification should take place more rapidly than the oxidation, so that the hydroperoxide formed is immediately removed in the stream of gas or steam.

The recovery of aromatic hydroperoxides, especially di-isopropyl benzol monohydroperoxide, from the solutions containing these aromatic peroxides, by steam distillation at reduced pressure, is known from German Published Specification No. 24 21 039. In so doing, it is considered preferable to separate the corresponding di-hydroperoxides before the steam distillation, since the thermal decomposition of these products must be taken into account.

Finally, United Kingdom Patent Specification No. 1 137 717 discloses a process for the purification of tertiary butyl hydroperoxide, which consists of extracting the material which is contaminated with di-tertiary butyl peroxide in water, heating the separated aqueous phase, and recovering the purified tertiary butyl hydroperoxide which is separated out in so doing.

The places in the literature indicated above, therefore, do not provide any suitable process with which one can succeed in a simple, economical, and safe manner in separating the desired tertiary alkyl hydroperoxides from the undesired di-tertiary alkyl peroxides resulting during their production.

The purpose of the present invention, therefore, consists of indicating such a separating process which makes it possible, especially, to dispense with the addition, which has been customary thus far, of the troublesome di-tertiary alkyl peroxides.

It was now found, surprisingly, that it is possible, by distillation in the presence of water at reduced pressure and at a temperature below about 45° C., to distill off the undesired di-tertiary alkyl peroxides, together with water, from the desired tertiary alkyl hydroperoxides and to isolate these with high yield and with high purity from the sump product.

The subject of the invention is, therefore, a process for the distillative separation of tertiary alkyl hydroperoxides of the general formula

R—OOH in which R stands for a tertiary alkyl group with 4 to 6 carbon atoms, and especially of tertiary butyl hydroperoxide and tertiary amyl hydroperoxide, from the corresponding di-tertiary alkyl peroxides resulting during their production. The process is characterized in that the reaction mixture resulting during the production of tertiary alkyl hydroperoxide is neutralized, if necessary, and subjected to vacuum distillation in the presence of water at a temperature of less than about 45° C., and the purified tertiary alkyl hydroperoxide is recovered as a sump product.

It has been shown that in spite of the danger of pure tertiary butyl hydroperoxide, because of the conditions used and, especially, because of the addition of water, the distillation becomes possible without danger. This must surprise the expert, since it is well known from the literature that explosions have already occured in the vacuum distillation of tertiary butyl hydroperoxide, so that it could not be expected that the distillative purification in the presence of water, according to the present invention, may be accomplished without problems and without danger.

In the distillation using the conditions according to the present invention, with the addition of water, therefore, the contaminating di-tertiary alkyl peroxide distills off together with hydroperoxide in the form of about a 50/50 mixture and forms an organic phase in the distillate that accumulates, separated from the water that has gone over, which is present as the aqueous phase. The purified hydroperoxide, which contains water (about 70%) remains behind in the sump, on the other hand, with a residual content of only about 0.2% di-tertiary alkyl peroxide.

It is preferable to carry out the vacuum distillation under such conditions that the temperature is kept below 40° C. Thus, the distillative separation of tertiary butyl hydroperoxide from di-tertiary butyl peroxide is preferably carried out at a temperature between 25° and 35° C., which corresponds to a pressure of about 22 to 55 mbar.

According to the present invention, the distillation fundamentally takes place with the use of a fairly strong vacuum, which is kept in about the range from 0 to 70 mbar.

In carrying out the process according to the present invention, the crude product provided for the distillation is first washed thoroughly free of acid. In washing, the addition of sodium bicarbonate for neutralization is also suitable, after which at least one additional washing is carried out.

This procedure has proved to be especially advantageous, because traces of acid that are still present in the crude product can catalyze the new formation of the undesired di-tertiary alkyl peroxide during the distillation.

The process according to the present invention can be carried out intermittently or, more preferably, continuously. In the continuous operation of the process preferred according to the present invention, the crude product to be separated is fed into the distilling apparatus continuously, and the distillate and the sump product are removed either continuously, or intermittently or discontinuously.

Investigations of the inflammability of tertiary butyl hydroperoxide-air mixtures have shown that if the concentration of the tertiary alkyl hydroperoxide in the sump is kept below about 70% by adding water, no mixtures that are inflammable in the vacuum are formed. With tertiary amyl hydroperoxide, the corresponding value is about 90% by weight.

Thus, the process according to the present invention makes it possible to separate tertiary alkyl hydroperoxides simply and safely from the undesired di-tertiary alkyl peroxides that are formed during their production, in which the desired tertiary alkyl hydroperoxides are obtained in a yield of up to 96%. At the same time, those products recovered from the sump product show a content of the undesirable di-tertiary alkyl peroxides of only 0.2 to 0.7% by weight.

The following examples serve for further explanation of the present invention.

EXAMPLE 1

This example illustrates the distillative separation of tertiary butyl hydroperoxide from the di-tertiary butyl peroxide that results during its production in a rectification apparatus that operates semicontinuously.

The crude product to be distilled is fed into the apparatus continuously, while the sump is tapped discontinuously, and the distillate is collected in a receiver.

A tertiary butyl hydroperoxide, which results during the synthesis, is used as the crude product. It contains about 20% di-tertiary butyl peroxide by weight.

The sump is charged with a 16% aqueous solution of the tertiary butyl hydroperoxide crude product. Then, after using a vacuum of 53±1.3 mbar, the temperature of the sump is broungt to 32° to 32.5° C., and one waits until the temperature at the top of the column has stabilized at 30° C. The work is carried out with the temperature of the cooling brine in the reflux condenser from −10° to −16° C. Then moist tertiary butyl hydroperoxide is continuously fed in in a quantity of 137 to 232 g/h. After the temperature at the top of the column has dropped to 29° C., the distillate is removed. The work is carried out at a distillate/reflux ratio of 1:4 to 1:10.

The results obtained in various tests are summarized in the table below.

TABLE

| Test No. | Charge of Moist Tertiary Butyl Hydroperoxide (g/h) | Reflux Ratio | Di-Tertiary Butyl Peroxide Content | | Tertiary Butyl Hydroperoxide Content in Distillate (%) | Tertiary Butyl Hydroperoxide Yield (%) |
| | | | Distillate (%) | Sump (%) | | |
|---|---|---|---|---|---|---|
| 1 | 232 | 1:4 | 37 | 0.27 | 56.0 | 91 |
| 2 | 212 | 1:4 | 35 | 0.20 | 57.2 | 91 |
| 3 | 223 | 1:9 | 52 | 0.35 | 43.3 | 96 |
| 4 | 218 | 1:9 | 54 | 0.31 | 41.8 | 96 |
| 5 | 176 | 1:7 | 28 | 0.18 | 62.0 | 91 |
| 6 | 188 | 1:10 | 40 | 0.19 | 53.7 | 95 |
| 7 | 181 | 1:9 | 84.6 | 0.65 | 14.4 | 96 |
| 8 | 186 | 1:6 | 78.8 | 0.4 | 20.0 | 93 |
| 9 | 173 | 1:3 | 60.0 | 0.5 | 37.0 | 85 |
| 10 | 172 | 1:6 | 77 | 0.23 | 21.4 | 93 |
| 11 | 181 | 1:3 | — | 0.42 | 31.5 | — |
| 12 | 137 | 1:4 | 62.3 | 0.2 | 34.6 | 83.5 |
| 13 | 141 | 1:8 | 75.0 | 0.2 | 23.3 | 90.3 |

It is evident from the table above that the di-tertiary butyl peroxide content in the sump drops when a large amount of distillate has been removed, but, at the same time, the yield of tertiary butyl hydroperoxide decreases. By increasing the heat and, at the same time, reducing the feed under strong reflux, both the yield and the quality of the product are improved.

In addition, it is evident that by reducing the amount fed in or the use of a longer or better column, it is possible to reduce the di-tertiary butyl peroxide content of the sump product to 0.2% by weight or less.

EXAMPLE 2

92% tertiary amyl hydroperoxide, containing 13 to 14 g/l of di-tertiary amyl peroxide, is put into the sump, and an equal amount of water is added. Then a vacuum of 35 mbar is used, and rectification is carried out at 26° C. At a temperature of 26° C. at the top and a ratio of reflux:removal=4:1, distillate was removed. Because of the low volatility of the tertiary amyl hydroperoxide and the di-tertiary amyl peroxide, the temperature of the cooling brine is not critical.

In the upper phase of the top product, the distillate contains 352 g/l of di-tertiary amyl peroxide; in the upper phase of the sump, 8 g/l of di-tertiary amyl peroxide was found.

It will be understood that the specification and examples are illustrative, but not limitative of the present invention and that other embodiments within the spirit and scope of the invention will suggest themselves to those skilled in the art.

What is claimed is:

1. Process for the production of tertiary alkyl hydroperoxides of the formula

R—OOH wherein

R is a tertiary alkyl group with 4 to 6 carbon atoms, which process comprises reacting the corresponding tertiary alkyl alcohol with the hydrogen peroxide to obtain the desired tertiary alkyl hydroperoxide including dialkylperoxide impurities, neutralizing the reaction mixture, subjecting same to vacuum distillation in the presence of water at a temperature of less than about 45° C., and recovering, as a bottoms product, the purified tertiary alkyl hydroperoxide in a yield of at least about 83.5%.

2. Process as claimed in claim 1 wherein R is tertiary butyl.

3. Process as claimed in claim 2 wherein the peroxide concentration in the bottom of the distillation column is kept below about 70% by weight by adding water.

4. Process as claimed in claim 1 wherein the distillation is carried out at a bottom temperature of less than 40° C.

5. Process as claimed in claim 1 wherein the separation is carried out at a bottom temperature of between 25° to 35° C. and a pressure of about 22 to 55 mbar.

6. Process as claimed in claim 1 wherein the raw product for distillation is first washed until it is free from acid, then neutralized with sodium carbonate and washed again.

7. Process as claimed in claim 6 wherein distillation of the raw product is carried out continuously.

8. Process as claimed in claim 7 wherein the distillate and bottoms product are removed intermittently.

9. Process as claimed in claim 1 wherein R is amyl.

10. Process as claimed in claim 9 wherein the peroxide concentration in the bottom of the distillation column is kept below about 90% by weight by adding water.

* * * * *